United States Patent [19]
Tillinghast

[11] Patent Number: 5,645,671
[45] Date of Patent: Jul. 8, 1997

[54] METHOD FOR MANUFACTURING COMPOSITE PADS

[75] Inventor: Ted Tillinghast, Cardiff-by-the-Sea, Calif.

[73] Assignee: Smith & Nephew DonJoy Inc., Carlsbad, Calif.

[21] Appl. No.: 366,676

[22] Filed: Dec. 30, 1994

[51] Int. Cl.$^6$ .............................. B32B 31/18; B32B 31/20
[52] U.S. Cl. .................. 156/222; 156/251; 156/274.4; 156/274.8; 156/275.1; 156/275.3; 156/308.4; 156/380.7; 156/380.8; 428/194
[58] Field of Search .................. 156/222, 380.7, 156/380.8, 251, 308.4, 275.1, 274.4; 602/26; 428/194, 246

[56] References Cited

U.S. PATENT DOCUMENTS

| | | |
|---|---|---|
| 3,063,448 | 11/1962 | Scholl . |
| 3,088,860 | 5/1963 | Scholl ........................ 156/222 |
| 4,430,069 | 2/1984 | Carlisle ....................... 156/583.3 |
| 5,240,538 | 8/1993 | Hyams et al. .................. 156/245 |

FOREIGN PATENT DOCUMENTS

| | | |
|---|---|---|
| 0486241 | 5/1992 | European Pat. Off. . |
| 4401849 | 8/1984 | Germany . |

Primary Examiner—Michele K. Yoder
Attorney, Agent, or Firm—Brown, Martin, Haller & McClain

[57] ABSTRACT

Disclosed is a method for manufacturing a composite pad from stock made of a relatively thin, sheet-like first layer, a relatively thin, sheet-like second layer and a relatively thick layer of an elastic, cushioning material sandwiched between the two. The outer layers are made of material, such as heat sealable material, that forms a seal under predetermined conditions. The pad is manufactured by first forming a sealed perimeter from the stock using a sealing tool and then using the same tool to separate the pad from the adjacent stock while simultaneously orienting the seal away from the side of the pad which will contact the wearer of a brace into which the pad is fitted.

16 Claims, 3 Drawing Sheets

METHOD FOR MANUFACTURING COMPOSITE PADS

BACKGROUND OF THE INVENTION

1. Field of the Invention

This invention relates to the mechanical arts. In particular, it relates to a method for manufacturing a composite pad and more particularly to a method for manufacturing a composite pad to be worn as part of an orthopedic brace and the pads produced by the method.

2. Discussion of the Related Art

Composite pads are used in great variety of environments. One particularly demanding environment is found where a composite pad is used to cushion an orthopedic brace.

Orthopedic braces are commonly worn to stabilize a skeletal joint that has been weakened by injury or other infirmity. The brace is typically made of a number of rigid structural components dynamically linked by hinges to support the joint when the wearer is active. The brace is positioned such that the hinges traverse the joint being stabilized, while the rigid components are secured to the body above and below the joint.

Pads are often used to cushion the contact between the body and the rigid components of the brace, because the pads conform to the body of the user and provide a soft barrier between the brace and the body. Typically, such pads are made of porous, resilient foams, such as a polyvinyl acetate or polyurethane foams. However, it has proven impractical and undesirable to make a pad consisting only of a porous foam. This is because the foam is readily degraded and can be abrasive when placed in direct contact with the wearer. Consequently, in the design of pads for orthopedic braces, it is a desideratum to include a layer of a durable, but soft, material compatible with the wearer to serve as an interface between the wearer and the foam. Further, as mentioned above, the pads are used in an environment where there is considerable movement. Not only does this contribute to the deterioration of the pad, but it has proven difficult to secure a foam directly to the brace in order to prevent the pad from being displaced. Consequently, it is also a desideratum to provide a backing to the pad that is both durable and specifically adapted to be secured to the brace.

It has also proved difficult to design a fully satisfactory and optimum pad having a foam material sandwiched between two outer layers. In order to ensure the structural integrity of such a pad, it is generally necessary to weld or otherwise seam the two layers along the perimeter of the pad. In the prior art, pads have been sealed or welded utilizing a die tool that produces a wide seal or weld. One reason for the wide seal or weld is to ensure that the pad may subsequently be cut or severed from the excess material along the resulting seam without compromising the effectiveness of the seal. Conventionally, this sharp or severing action has been accomplished by use of a separate tool. As a result, substantial tolerances must be provided to account for film stretching, variations in machine operation, and registration between the sharp tool and the seal. Unfortunately, the resulting seam not only tends to be unsightly, but can cause discomfort as it chafes against the wearer.

Other prior art pads have a seam formed by sewing a bias tape that is folded over the edges of the outer layers. Pads of this construction can be less durable, less attractive to the eye and require more manufacturing time. In addition the bias tape can irritate the wearer.

Accordingly, there has existed a need for a simple and effective method for manufacturing a composite pad that provides significant cushioning and is durable, but has a layer providing a smooth, pliable surface for contacting the wearer, and is effectively sealed along the perimeter of the pad to a second layer for securing the pad to the brace. There has existed a further need for a method for sealing the two layers in such a manner that the resulting seam is not unsightly and does not irritate the wearer. There has existed a still further need for the pads formed by such methods. The present invention satisfies these and other needs and provides further related advantages.

SUMMARY OF THE INVENTION

The present invention is embodied in a novel method for making a composite pad having an improved perimetrical seal or weld between its outer layers. The method is particularly adapted to the manufacture of composite pads to be worn with an orthopedic brace.

The pad is formed from a relatively thin, sheet-like first layer and, generally opposing the first layer, a relatively thin, sheet-like second layer. The first and second layers are selected from materials that form a seal with one another when the layers come into contact under predetermined conditions. Sandwiched between these two layers is a relatively thick layer of a soft, cushioning material. When the pad is to be used as part of an orthopedic brace the first layer is chosen to provide a durable surface for securing the pad to the brace and the second layer is chosen to provide a soft, but durable material for contacting the wearer.

In the initial step, the stock is positioned so that the first layer rests on a deformable, resilient sealing surface. Next a sealing tool having a die with a sharp edge shaped to define the perimeter of the pad is aligned above the second layer and then the sharp edge is caused to engage the stock. As the die presses against the stock, it causes a portion of the second layer corresponding to the perimeter of the finished pad to displace a portion of the cushioning material and then contact a portion of the first layer under conditions such that a sealed perimeter is formed.

For example, in some embodiments the die is heatable. In some of these embodiments, the sealing tool is an RF welding tool and the sealing surface is a nonconducting material, such as silicon, covering an RF weld table. In these embodiments, the first and second layers can be made of a thermoformable, heat-sealable material and the die is heated by the RF energy to a temperature sufficient to cause the first and second layers to soften and form a seal when they come into contact with one another. Alternatively, the first and second layers can be bound to the cushioning material using a heat-reactivatable adhesive and the adhesive then heated by the die to a temperature sufficient to cause a seal between the first and second layers when they come into contact.

In the next step, the pad is severed from the adjacent stock using the same die while maintaining the die in the same alignment as was used to seal the pad.

Other features and advantages of the present invention will become apparent from the following description of the preferred embodiments, taken in conjunction with the accompanying drawings, which illustrate, by way of example the principles of the invention.

DESCRIPTION OF THE PREFERRED EMBODIMENTS

Figure 1:
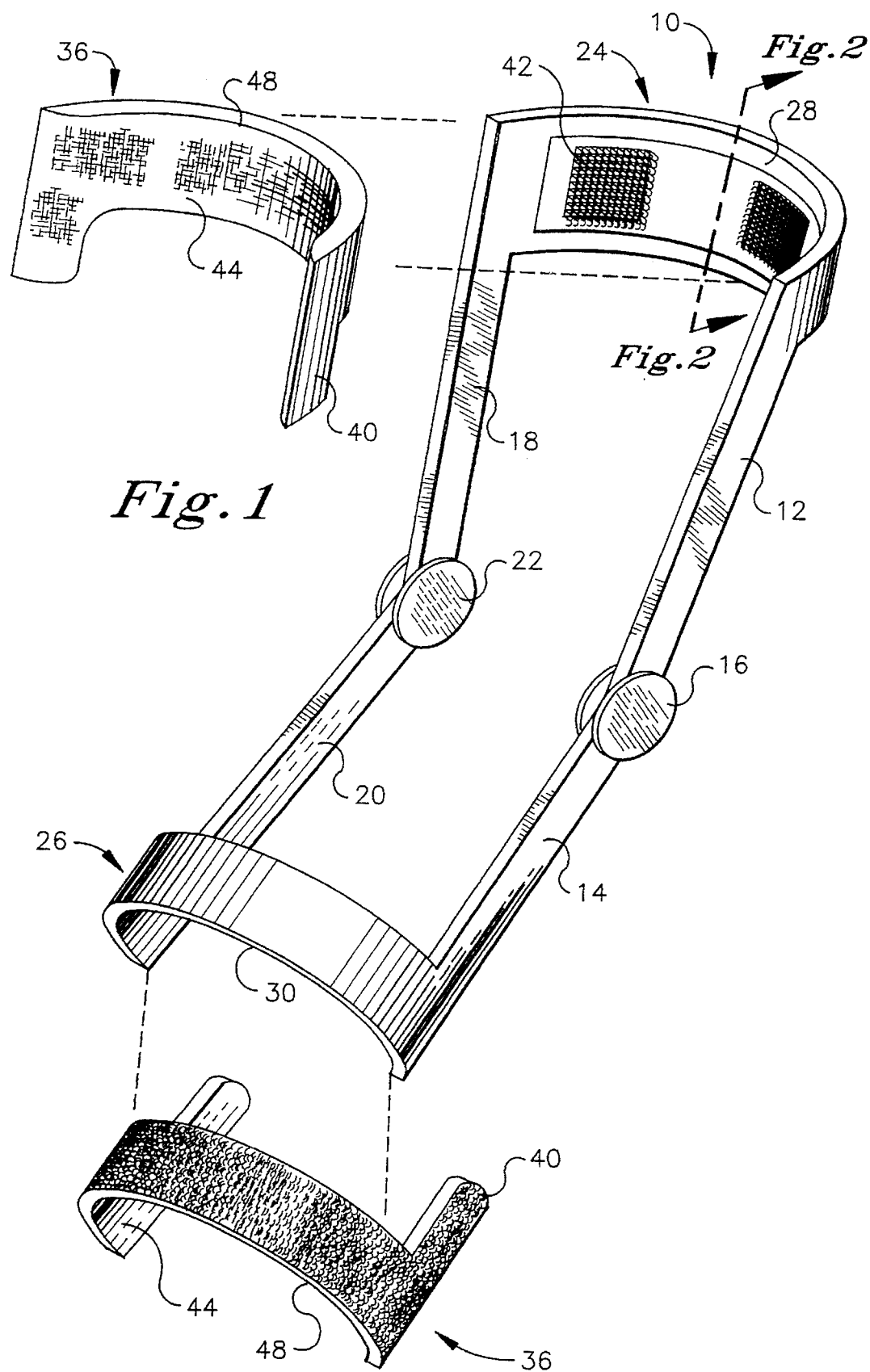
FIG. 1 is a perspective view, showing in a spaced apart relationship, a knee brace that incorporates pads manufactured by a process in accordance with the invention.

With reference to the exemplary drawings and particularly to FIG. 1, there is shown an orthopedic brace 10. The particular orthopedic brace 10, shown by way of example, is a knee brace of conventional design having a plurality of rigid structural components including medial upper and lower arms 12, 14, a medial hinge 16, lateral upper and lower arms 18, 20, a lateral hinge 22, an upper leg cuff 24, and a lower leg cuff 26. Upper and lower leg cuffs 24 and 26 both have a similar curved shape providing them with concave inner surfaces 28 and 30. Preferably the cuffs 24 and 26 are bendable to conform to the leg of the wearer.

Shown in a spaced apart relationship to brace 10 are generally U-shaped pads 36. The pads are shaped to conform to concave inner surfaces 28 and 30, respectively, and provide a cushion between the brace's rigid structural components and the wearer.

Figure 2:
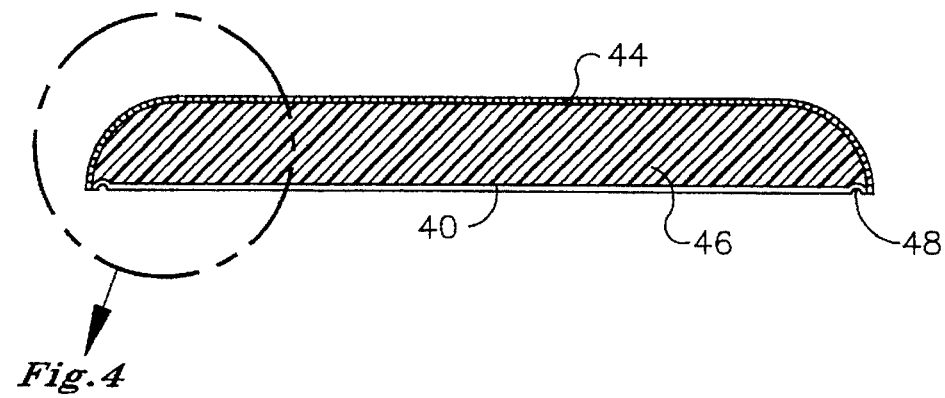
FIG. 2 is a cross-sectional view of a pad manufactured by a process in accordance with the invention.

Referring additionally to FIG. 2, the pads 36 each have a relatively thin, sheet-like first layer 40. This layer is made of a durable, easily washable material which enables removable fastening of the pads to the brace. A preferred fastener is a hook and loop fastener, such as the material available under the trademark Velcro. The first layer is made of material having Velcro™ loops on its outer surface and strips of material 42 (only one shown) containing complimentary Velcro™ hooks are affixed to the inner surfaces 28 and 30 of the cuffs. It is to be understood that the positions of the hook and loop components can be reversed such that the hook component forms the outer surface of the first layer and the loop component is affixed to the inner spaces. Alternatively, the pads are removably fastened to the inner spaces using other conventional means, such as screws in combination with internally threaded rivets.

Generally opposing the first layer is a relatively thin, sheet-like second layer 44 of about the same configuration. The second layer is made from a soft, pliable material that is resistant to wear, washable, smooth and provides a comfortable surface for contacting the wearer.

Sandwiched between the first and second layers 40 and 44 is a relatively thick layer 46 formed from a soft cushioning material. Preferably, the first and second layers are uniformly bonded to the cushioning material by a suitable adhesive or by flame lamination.

A perimetrical seal 48 formed between the first and second layers 40 and 44 ensures the integrity of the composite pad. Preferably, the first layer can be laid flat, while the second layer is wrapped around the edge of the cushioning material to meet the second layer. It is a distinct advantage of the method in accordance with the invention that the seals are located away from the surface that contacts the wearer and that the seals are oriented in a direction that does not face the wearer, and preferably faces away from the wearer. Such a location and orientation virtually eliminates the possibility of the seals chafing against the wearer.

Figure 3C:
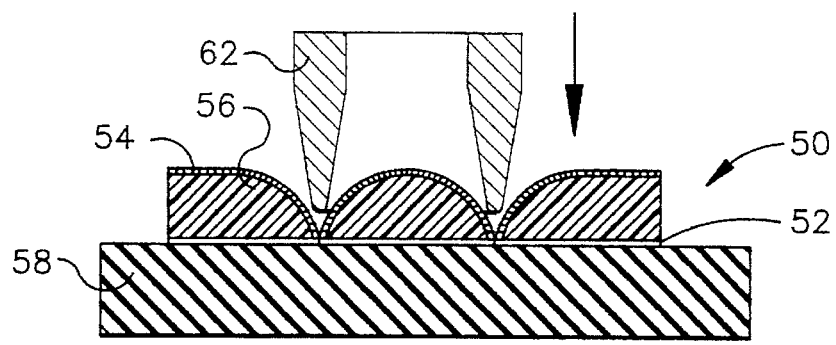
FIGS. 3a–c are partially cut away, front elevational views of a portion of the apparatus and starting material illustrating the steps for manufacturing a pad in accordance with the invention.
Figure 3A:
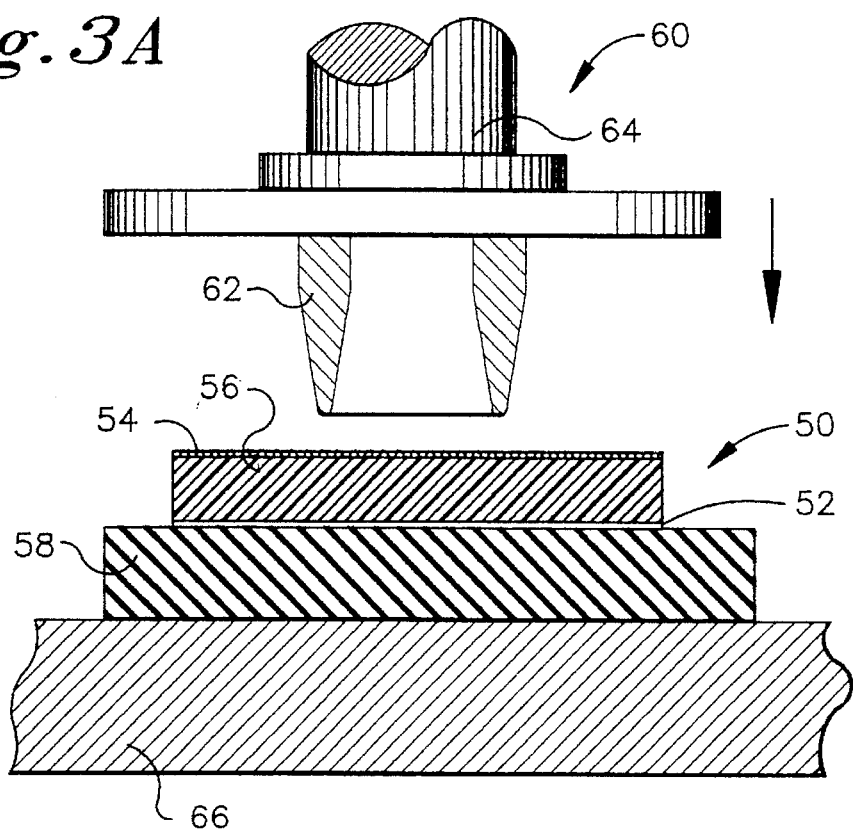
Figure 3B:
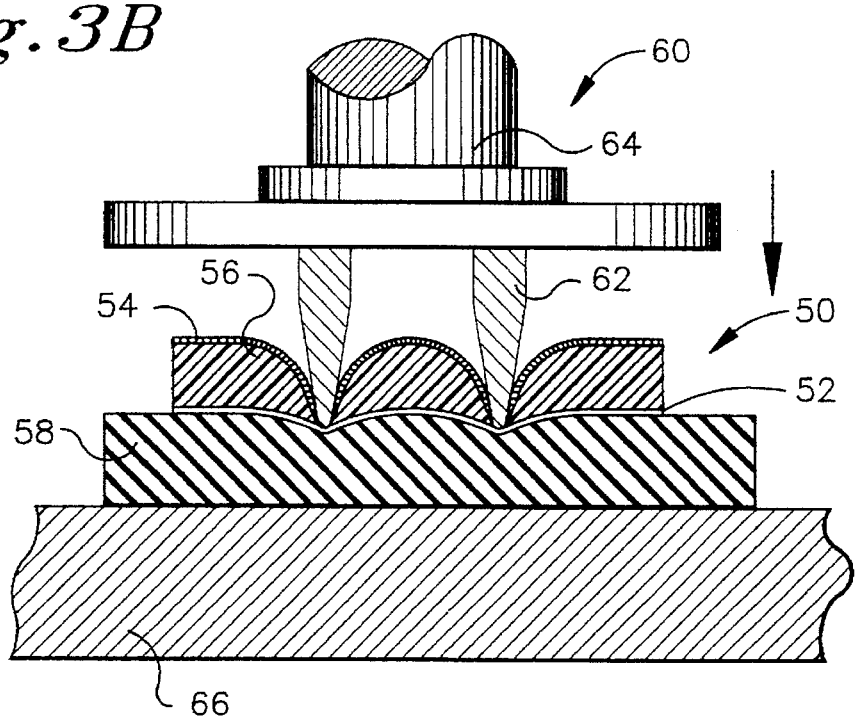

Turning now to the manufacture of such pads, the sealing or welding and then severing of a stock 50 to make a composite pad is shown in FIGS. 3a–c. The stock is formed of a relatively thin, sheet-like first layer 52 that provides the surface for securing the pad to the brace when the pad is formed. Generally opposing the first layer is a soft, pliable, relatively thin, sheet-like second layer 54 that provides the surface for contacting the wearer when the pad is formed. Sandwiched between these two layers is a relatively thick layer of an elastic, cushioning material 56.

The first and second layers can be the of the same or different material. They are selected from materials that form a seal with one another when the layers come into contact under predetermined conditions, such as when sufficient heat and pressure is applied to the layers. Accordingly, in some embodiments, the first and second layers are advantageously made from thermoformable, heat-sealable materials. Representative heat-sealable materials include polyurethane, including combination polyurethane-cotton weaves, nylon and rayon. Particularly useful materials for making the layer having a surface for securing the pad to the brace include nylon-based fastenable loop or hook materials. Particularly useful materials for making the layer having a surface for contacting the wearer include synthetic chamois, a combination polyurethane-cotton weave, and Doeskin™, a nylon weave.

Alternatively, the first and second layers can be made from materials, such as cotton, which are not necessarily heat sealable. In such embodiments, the first and second layers are bonded to the cushioning material using a heat reactivatable adhesive such as a urethane-based adhesive.

Although the cushioning layer 56, like the first and second layers 52 and 54, is formed from an elastic material, the cushioning material is generally thicker and substantially less pliable than the material of the first and second layers. The cushioning layer is typically formed from any elastomeric thermoformable foam. Representative foams include polyvinyl acetate and polyurethane foams having a thickness of about ⅛ inch or more.

As best seen in FIG. 3a, during the initial step, the stock 50 is positioned so that the first layer 52 rests on a deformable, resilient seal surface 58 compatible with high temperature sealing processes. Next, a sealing tool 60 having a die 62 with a sharp edge shaped to define the perimeter of the pad is aligned above the second layer 54.

As shown in FIG. 3b, the die 62 is then caused to engage the stock 50. As the sealing tool presses against the stock it causes a portion of the second layer 54 corresponding to the perimeter of the finished pad to displace a portion of the cushioning material 56 while also causing the sealing pad 58 to deform and ultimately causing the second layer to contact a portion of the first layer. The conditions are such that a sealed perimeter is formed when the two layers contact one another.

Generally, the lower the durometer of the sealing pad 58 and the greater the pressure applied by the die 62, the more the pad deforms. The more the pad deforms, the more of the second layer 54 that is caused to displace the cushioning material 56 and the closer the seam is formed to the plane of the surface of the first layer 52.

In the embodiment, shown in FIGS. 3a–c, the sealing tool is an RF welding tool that includes weld head 64 and the sealing surface 58 is made of a nonconducting material, such as silicon, covering an RF weld table 66. To further ensure that there is no arcing when the sharp edge of die 62 is moved toward the RF weld table, a melamine coating (not shown) is interposed between the pad and the weld table.

Finally, as seen in FIG. 3c, additional pressure is applied to the die 62 and the sharp edge severs the pad from the adjacent stock. As shown in FIG. 3c, this step is facilitated if the deformable sealing surface is removed, and replaced with a hard cutting surface. Alternatively, the sealing tool and sealed pad are moved and positioned above a clicker table. In either case, the die 62 is maintained in the alignment used to seal the pad.

Figure 4:
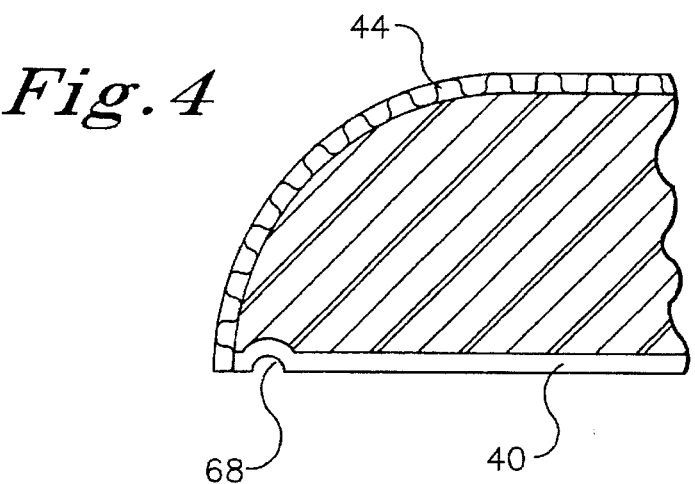
FIG. 4 is an enlarged view of a portion of the pad shown in FIG. 2.

FIG. 4 illustrates the unique seal that is formed by the process in accordance with the invention. By using the same die to both weld the first and second layers 40 and 44 and then to sever the resulting pad from the adjacent stock a seal having a dimple 68 is produced. The dimple is not only located away from the second surface, but it orients the seal in the direction towards the first surface. By controlling the initial orientation of the stock on the sealing surface, as well as the durometer of the sealing pad and the pressure applied by the sealing tool, it is possible to control the relative location and orientation of the seal. In the embodiment shown in the FIGS. 2 and 4, the conditions were chosen so that the seal is located away from the surface that contacts the wearer and in a direction facing away from the wearer. Such a location and orientation virtually eliminates the possibility of the seal chafing against the wearer of an orthopedic brace.

I claim:

1. A method for manufacturing a composite pad to be worn with an orthopedic brace comprising the steps of:

forming a sealed perimeter of the pad from a stock comprising:
a relatively thin first sheet having a surface for contacting the brace when the pad is formed,
a relatively thin second sheet having a surface for contacting the wearer when the pad is formed, the second sheet generally opposing the first sheet, the first and second sheets being sealable to one another when the sheets contact one another under predetermined conditions, and
a relatively thick layer of a soft, cushioning material disposed between the first and second sheets, by positioning the stock on a deformable, resilient sealing surface, such that the first sheet adjoins the sealing surface with the cushioning material and the second sheet extending outwardly from the sealing surface;

aligning a sealing tool above the second sheet, the sealing tool having a sharp edge shaped to define the perimeter of the pad;

pressing the sealing tool against the stock to cause a portion of the second sheet to displace a portion of the cushioning material, the sealing tool thereafter causing the second sheet to contact a portion of the first sheet to form a seal around the perimeter of the pad oriented away from the second sheet and in the direction of the first sheet; and then severing the pad from the adjacent portions of the stock with the same sharp edge while maintaining the sealing tool in the alignment used to seal the pad.

2. The method of claim 1 wherein the sharp edge is heatable.

3. The method of claim 2 wherein the sealing tool is an RF welding tool that heats the sharp edge with RF energy and the sealing surface is a nonconducting material covering an RF weld table.

4. The method of claim 2 wherein the first sheet is made of a heat-sealable material, the second sheet is made of a heat-sealable material and the sharp edge is heated to a temperature sufficient to cause a seal to be formed when the first sheet contacts the second sheet.

5. The method of claim 2 wherein the first sheet is bonded to the cushioning material with a heat reactivatable glue, the second sheet is bonded to the cushioning material with a heat reactivatable glue, and the sharp edge is heated to a temperature sufficient to cause a seal to be formed by thermal activation of the glue when the first sheet contacts the second sheet.

6. The method of claim 3 wherein the first sheet is made of a heat-sealable material, the second sheet is made of a heat-sealable material and the sharp edge is heated to a temperature sufficient to cause a seal to be formed when the first sheet contacts the second sheet.

7. The method of claim 3 wherein the first sheet is bonded to the cushioning material with a heat reactivatable glue, the second sheet is bonded to the cushioning material with a heat reactivatable glue, and the sharp edge is heated to a temperature sufficient to cause a seal to be formed by thermal activation of the glue when the first sheet contacts the second sheet.

8. The method of claim 6 wherein the first and second sheets are made from thermoformable materials.

9. The method of claim 8 wherein the materials are formed from polyurethane, rayon or nylon.

10. The method of claim 6 wherein the first sheet is securable to the brace.

11. The method of claim 10 wherein the first sheet comprises one of the components of a hook and loop fastening material.

12. The method of claim 6 wherein the cushioning material is made from a thermoformable foam.

13. The method of claim 12 wherein the thermoformable foam is a polyvinyl acetate or polyurethane foam.

14. The method of claim 13 wherein the sealing surface is made of silicone.

15. A method for manufacturing a composite pad to be worn with an orthopedic brace comprising the steps of:

forming a sealed perimeter of the pad from a stock comprising:
a relatively thin first sheet made of a thermoformable, heat-sealable material, the first sheet having a surface for contacting the brace when the pad is formed,
a relatively thin second sheet made of a thermoformable, heat-sealable material, the second sheet having a surface for contacting the wearer when the pad is formed and the second sheet generally opposing the first sheet, and
a relatively thick layer of a thermoformable, elastic foam disposed between the first and second sheet, by positioning the stock on a nonconductive, deformable, resilient sealing surface covering an RF weld table, such that the first sheet adjoins the sealing surface with the cushioning layer and the second sheet extending outwardly from the sealing surface;

aligning a sealing tool above the second sheet, the sealing tool having a sharp edge shaped to define the perimeter of the pad, the sharp edge heatable by RF energy;

pressing the sealing tool against the stock to cause a portion of the second sheet to displace a portion of the cushioning material, the sealing tool thereafter causing the second layer to contact a portion of the first sheet to form a seal around the perimeter of the pad oriented away from the second sheet and in the direction of the first sheet; and then severing the pad from the adjacent portions of the stock with the same sharp edge while maintaining the sealing tool in the alignment used to seal the pad.

16. A method as in claim 1 wherein said pressing of said sealing tool against said stock further includes forming a dimple in said seal which facilitates said orientation of said seal away from said second sheet and in the direction of said first sheet.

* * * * *